United States Patent
Yamamoto

(10) Patent No.: US 8,925,607 B2
(45) Date of Patent: Jan. 6, 2015

(54) ULTRASONIC JOINING APPARATUS AND ABSORBENT ARTICLE MANUFACTURING APPARATUS

(75) Inventor: Hiroki Yamamoto, Kagawa (JP)

(73) Assignee: Unicharm Corporation, Ehime-ken (JP)

( * ) Notice: Subject to any disclaimer, the term of this patent is extended or adjusted under 35 U.S.C. 154(b) by 339 days.

(21) Appl. No.: 13/383,430

(22) PCT Filed: Jul. 30, 2010

(86) PCT No.: PCT/JP2010/062934
§ 371 (c)(1),
(2), (4) Date: Mar. 22, 2012

(87) PCT Pub. No.: WO2011/013816
PCT Pub. Date: Feb. 3, 2011

(65) Prior Publication Data
US 2012/0168084 A1    Jul. 5, 2012

(30) Foreign Application Priority Data

Jul. 31, 2009 (JP) ................. 2009-180195

(51) Int. Cl.
*B32B 37/00* (2006.01)
*A61F 13/15* (2006.01)
(Continued)

(52) U.S. Cl.
CPC ......... *A61F 13/15739* (2013.01); *B29C 65/086* (2013.01); *B29C 65/18* (2013.01);
(Continued)

(58) Field of Classification Search
CPC .... B29C 65/08; B29C 65/083; B29C 65/086; B29C 66/91; B29C 66/9121; B29C 66/91211; B29C 66/91212; B29C 66/91213; B06B 3/00; B23K 20/10

USPC ............ 156/73.1, 359, 553, 555, 580, 580.1, 156/580.2, 582
See application file for complete search history.

(56) References Cited

U.S. PATENT DOCUMENTS 5,059,277 A    10/1991   Willhite, Jr. et al.
7,060,142 B2 *  6/2006   Yamamoto .................. 156/73.1
(Continued)

FOREIGN PATENT DOCUMENTS

CN    1557628 A    12/2004
JP    59039514 A    3/1984
(Continued)

OTHER PUBLICATIONS

Office Action mailed Jun. 4, 2013 corresponds to Japanese patent application No. 2009-180195.

(Continued)

*Primary Examiner* — James Sells
(74) *Attorney, Agent, or Firm* — Lowe Hauptman & Ham LLP

(57) ABSTRACT

An anvil has a temperature adjustment mechanism including a heater. The anvil has a heat transmitter transmitting heat generated by the temperature adjustment mechanism. The anvil has a temperature sensor detecting a temperature of an anvil attachment portion in which the anvil of rotating drum installed. The ultrasonic joining apparatus includes a controller configured to control a temperature to which the rotating drum should be heated by the temperature adjustment mechanism. The controller controls a heat generation amount of the temperature adjustment mechanism on the basis of a detection result by the temperature sensor. The temperature adjustment mechanism and the heat transmitter are installed in each of the multiple anvils.

10 Claims, 10 Drawing Sheets

(51) Int. Cl.
*B29C 65/08* (2006.01)
*B29C 65/18* (2006.01)
*B29C 65/00* (2006.01)
*B29C 65/72* (2006.01)
*B29L 31/48* (2006.01)
*B29C 65/30* (2006.01)

(52) U.S. Cl.
CPC ........... *B29C 66/1122* (2013.01); *B29C 66/223* (2013.01); *B29C 66/3472* (2013.01); *B29C 66/43129* (2013.01); *B29C 66/81427* (2013.01); *B29C 66/81433* (2013.01); *B29C 66/81469* (2013.01); *B29C 66/8167* (2013.01); *B29C 66/83511* (2013.01); *B29C 66/83517* (2013.01); *B29C 66/91212* (2013.01); *B29C 66/91231* (2013.01); *B29C 66/91423* (2013.01); *B29C 65/72* (2013.01); *B29C 66/92611* (2013.01); *B29C 66/8181* (2013.01); *B29C 66/232* (2013.01); *B29L 2031/4878* (2013.01); *B29C 65/305* (2013.01); *B29C 66/21* (2013.01)
USPC ......... 156/359; 156/553; 156/555; 156/580.2

(56) References Cited

U.S. PATENT DOCUMENTS

| | | |
|---|---|---|
| 2005/0145317 A1 | 7/2005 | Yamamoto |
| 2006/0169387 A1 | 8/2006 | Nayar et al. |
| 2007/0251643 A1 | 11/2007 | Umebayashi et al. |

FOREIGN PATENT DOCUMENTS

| | | |
|---|---|---|
| JP | 6173502 U | 5/1986 |
| JP | 62270320 A | 11/1987 |
| JP | 6009927 A | 2/1994 |
| JP | 2003306865 A | 10/2003 |
| JP | 2004298413 A | 10/2004 |
| JP | 2008526552 A | 7/2008 |
| WO | 2005105410 A1 | 11/2005 |

OTHER PUBLICATIONS

Office Action dated Nov. 21, 2013, corresponds to Chinese patent application No. 201080033963.1.
Office Action dated Nov. 27, 2013, corresponds to Eurasian patent application No. 201200172/31.
International Search Report and Written opinion for PCT/JP2010/062934 dated Aug. 24, 2010.
Office Action issued Oct. 8, 2013, corresponds to Mexican patent application No. MX/a/2012/001314.
Office Action dated Jul. 31, 2014, corresponds to Chinese patent application No. 201080033963.1.

* cited by examiner

US 8,925,607 B2

ULTRASONIC JOINING APPARATUS AND ABSORBENT ARTICLE MANUFACTURING APPARATUS

RELATED APPLICATIONS

The present application is a National Phase of International Application Number PCT/JP2010/062934, filed Jul. 30, 2010 and claims priority from Japanese Application Number 2009-180195, filed Jul. 31, 2009.

TECHNICAL FIELD

The present invention relates to an ultrasonic joining apparatus for joining a first web and a second web, and an absorbent article manufacturing apparatus for manufacturing a pants-type absorbent article by joining the first web to form a front waistline portion and the second web to form a back waistline portion.

BACKGROUND ART

An absorbent article such as a disposable diaper generally includes: a front waistline portion to be fitted to the front waist of a wearer; a back waistline portion to be fitted to the back waist of the wearer; a crotch portion to be fitted to the crotch of the wearer; and leg-surrounding opening portions which open at both sides of the crotch portion. The front waistline portion and the back waistline portion are joined to each other at waist lateral-side portions.

In the steps of manufacturing a disposable diaper, a web is folded into two at the crotch portion by overlapping its first web to form the front waistline portion and its second web to form the back waistline portion with each other, and the web thus folded is joined at the left and right waist lateral-side portions, thereby forming the web into pants-type diapers. Here, ultrasonic joining using an ultrasonic joining apparatus is employed for the joining of the web at the left and right waist lateral-side portions (for example, Patent Document 1).

The ultrasonic joining apparatus includes: a rotating drum having an anvil formed thereon, the anvil being configured to form a joint pattern by which the front waistline portion and the back waistline portion are joined at the left and right waist lateral-side portions; and an ultrasonic horn configured to generate ultrasonic waves. The ultrasonic joining apparatus joins the first and second webs of the web, which is folded into two at the crotch portion, by pressing the ultrasonic horn intermittently against certain positions of the left and right waist lateral-side portions of the first and second webs while conveying the first and second webs between the rotating drum and the ultrasonic horn in a machine direction in parallel with a conveyance direction.

The anvil includes: a base being provided on the outer peripheral surface of the rotating drum; a projection being provided on the base and protruding in a normal direction of the rotating drum; and multiple protrusions protruding from the projection in the normal direction. When the ultrasonic horn is pressed against the anvil with the web interposed therebetween, the web is melted by being heated from the inside thereof, and is pressed against the protrusions protruding from the projection. As a result, a convexo-concave joint pattern is formed on the web.

An output value of the ultrasonic horn is adjusted to be suitable to the type and thickness of the web. Moreover, a clearance between each of the multiple protrusions and the ultrasonic horn is set to be small enough to apply ultrasonic vibration on the web, and large enough not to cut the web.

Further, the anvil of the conventional ultrasonic joining apparatus is provided with a heater and a temperature sensor, thereby maintaining a constant temperature condition in the ultrasonic joining. With the above manner, the ultrasonic joining can be performed appropriately on the web.

In an ultrasonic joining apparatus disclosed in Patent Literature 1 in which multiple anvils are provided on the outer peripheral surface of one rotating drum, the peripheral length of the metal-made rotating drum slightly changes and the radial length thereof also changes if the temperature of the apparatus changes between phases where the ultrasonic joining apparatus starts its operation and where the apparatus continuously runs. In addition, all the anvils provided on the rotating drum never wear down at the same condition, and thus the amount of wear attributable to the repetitive use is different from one anvil to another.

In consideration of the above factors, a clearance between each protrusion of the anvil and the ultrasonic horn is different from one anvil to another. In the conventional ultrasonic joining apparatus, the magnitude of ultrasonic vibration and the temperature condition can be set as one of conditions allowing ultrasonic joining of the web. However, in the conventional ultrasonic joining apparatus, the clearance adjustment needs to be made frequently in order to maintain stable ultrasonic joining quality.

However, as described above, a clearance between the tip of each protrusion of the anvil and the ultrasonic horn is different from one anvil to another, thus making the clearance adjustment work extremely troublesome. Further, the frequent suspension of a manufacturing line for the clearance adjustment is impractical. To cope with this, a large tolerance for the clearances has been employed.

PRIOR ART DOCUMENT

Patent Document

[Patent Document 1] Japanese Patent Application Publication No. 2004-298413 (paragraph [0044] and so forth)

SUMMARY OF INVENTION

An ultrasonic joining apparatus according to a first aspect includes: a rotator made of a member to be expanded or contracted by heat; a plurality of anvils provided at predetermined intervals in a rotation direction of the rotator; an ultrasonic horn configured to output ultrasonic vibrations; and a temperature adjustment mechanism configured to adjust a temperature of the rotator. The rotator and the ultrasonic horn are arranged to face each other with an intermediate web being conveyed therebetween, the intermediate web including a continuous first web and a continuous second web overlapping with each other. Each of the anvils and the ultrasonic horn pinch a certain region of the intermediate web to perform ultrasonic joining on the certain region.

DESCRIPTION OF EMBODIMENTS

Next, an embodiment of an ultrasonic joining apparatus and an absorbent article manufacturing apparatus according to the present invention is described with reference to the accompanying drawings. Note that, in the following description of the drawings, same or similar reference signs denote same or similar portions. In addition, it should be noted that the drawings are schematic and ratios of dimensions and the like are different from actual ones. Therefore, specific dimensions and the like should be determined in consideration of the following description. Moreover, the drawings also include portions having different dimensional relationships and ratios from each other.

(Structure of Absorbent Article)

Figure 1:
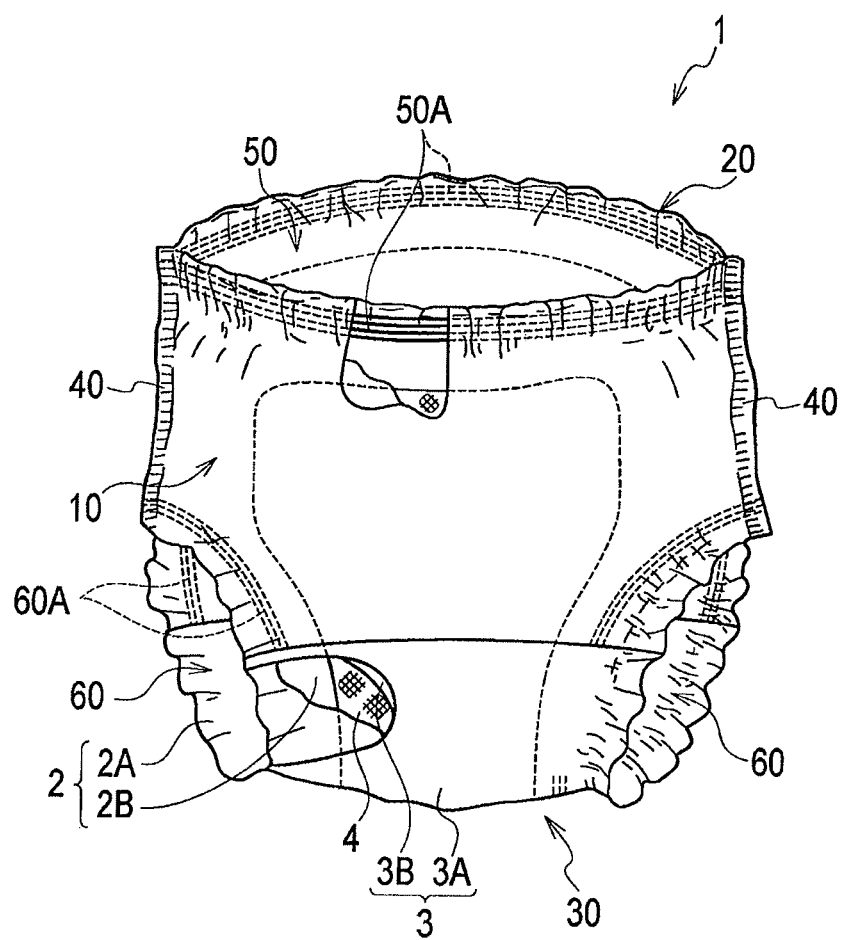
FIG. 1 is a perspective view showing an absorbent article according to an embodiment.

With reference to the drawing, description is first given of a structure of an absorbent article 1 manufactured by using an ultrasonic joining apparatus according to this embodiment. FIG. 1 is a perspective view showing the absorbent article 1 according to this embodiment.

In this embodiment, the absorbent article 1 is a disposable pants-type diaper. As shown in FIG. 1, the absorbent article 1 mainly includes a topsheet 2, a bottomsheet 3, and an absorber 4.

The topsheet 2 is provided at the innermost of the absorbent article 1 and to come into contact with the skin of a wearer. The topsheet 2 includes a top sheet 2A to come into contact with the wearer and a second sheet 2B joined to a surface, on the absorber 4 side, of the top sheet 2A. Note that, the topsheet 2 is made of a liquid permeable sheet such as a nonwoven fabric or perforated plastic film.

The backsheet 3 is provided at the outermost (on a side away from the wearer) of the absorbent article 1. The backsheet 3 includes a back sheet 3A provided at the outermost of the absorbent article 1 and a waterproof sheet 3B joined to a surface, on the absorber 4 side, of the back sheet 3A. Note that, the back sheet 3A is made of a nonwoven fabric or the like. The waterproof sheet 3B is made of a liquid impermeable sheet or the like.

The absorber 4 is provided between the topsheet 2 (the second sheet 2B) and the bottomsheet 3 (the waterproof sheet 3B), and absorbs bodily waste from the wearer.

The absorbent article 1 with the above structure is formed in combination of a front waistline portion 10 to be fitted to the front waist of the wearer, a back waistline portion 20 to be fitted to the back waist of the wearer, and a crotch portion 30 to be fitted to the crotch of the wearer (so-called three-piece type).

In the waist lateral-side portions of the wearer, the front waistline portion 10 and the back waistline portion 20 are joined at joint portions 40, and thereby form a waist opening portion 50 into which the body of the wearer is inserted. The crotch portion 30 is provided between the front waistline portion 10 and the back waistline portion 20. A waist gather 50A made of a stretchable rubber cord is provided to an entire peripheral edge of the waist opening portion 50. Leg-surrounding opening portions 60, into which the legs of the wearer are inserted, are formed on both sides of the crotch portion 30. A leg gather 60A made of a stretchable rubber cord is provided to an entire peripheral edge of each leg-surrounding opening portion 60.

(Method of Manufacturing Absorbent Article)

Figure 2:
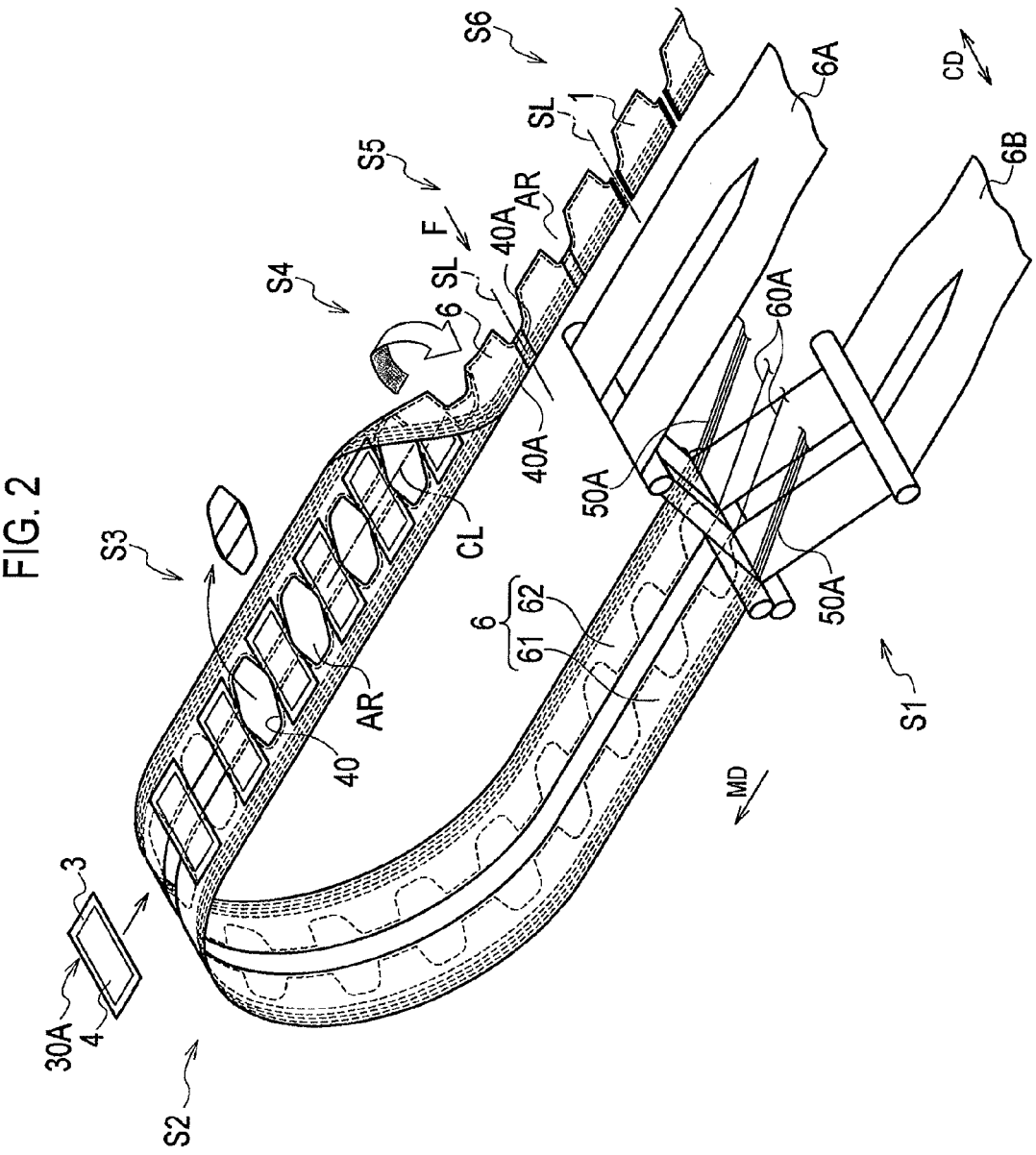
FIG. 2 is a diagram for explaining a part of a method of manufacturing the absorbent article according to this embodiment.

Next, a method of manufacturing an absorbent article according to this embodiment is described with reference to the drawing. FIG. 2 is a diagram for explaining a part of the method of manufacturing an absorbent article according to this embodiment.

As shown in FIG. 2, the method of manufacturing an absorbent article includes at least a waistline portion forming step S1, a crotch member transferring step S2, a leg-surrounding portion forming step S3, a folding step S4, a joining step S5, and a cutting step S6.

In the waistline portion forming step S1, gathers (the waist gather 50A and the leg gather 60A) are placed between a web 6A and a web 6B, and thereby a pair of webs 61 and 62 respectively prepared to form the front waistline portion 10 and the back waistline portion 20 are formed.

In the crotch member transferring step S2 after (downstream of) the waistline portion forming step S1, a crotch portion member 30A to form the crotch portion 30 is transferred (placed) between the pair of webs 61 and 62 at predetermined intervals in a machine direction MD.

In the leg-surrounding portion forming step S3 after (downstream of) the crotch member transferring step S2, a part of the webs 61 and 62 (the webs 6A and 6B) and a part o the backsheet 3 forming the crotch portion member 30 is cut. In other words, a gap AR to form the leg-surrounding opening portions 60 is formed in the webs 61 and 62.

In the folding step S4 after (downstream of) the leg-surrounding portion forming step S3, the web is folded into two by overlapping the web 61 on one side thereof and the web 62 on the other side thereof with each other along a folding line which is defined in the crotch portion member 30A and in parallel with the machine direction MD.

In the joining step S5 after (downstream of) the folding step S4, the front waistline portion 10 and the back waistline portion 20 are joined in joint regions 40A prepared to form the joint portions 40 by ultrasonic treatment or thermal treatment. The joint regions 40A are formed on both sides of an imaginary line SL indicating a to-be-cut position extending in a cross direction CD of an intermediate web 6.

In the cutting step S6 after (downstream of) the joining step S5, the intermediate web 6 joined in the joint regions 40A is cut in the machine direction MD at predetermined intervals, that is, along the imaginary line SL, whereby absorbent articles 1 are manufactured.

(Ultrasonic Joining Apparatus)

Figure 3:
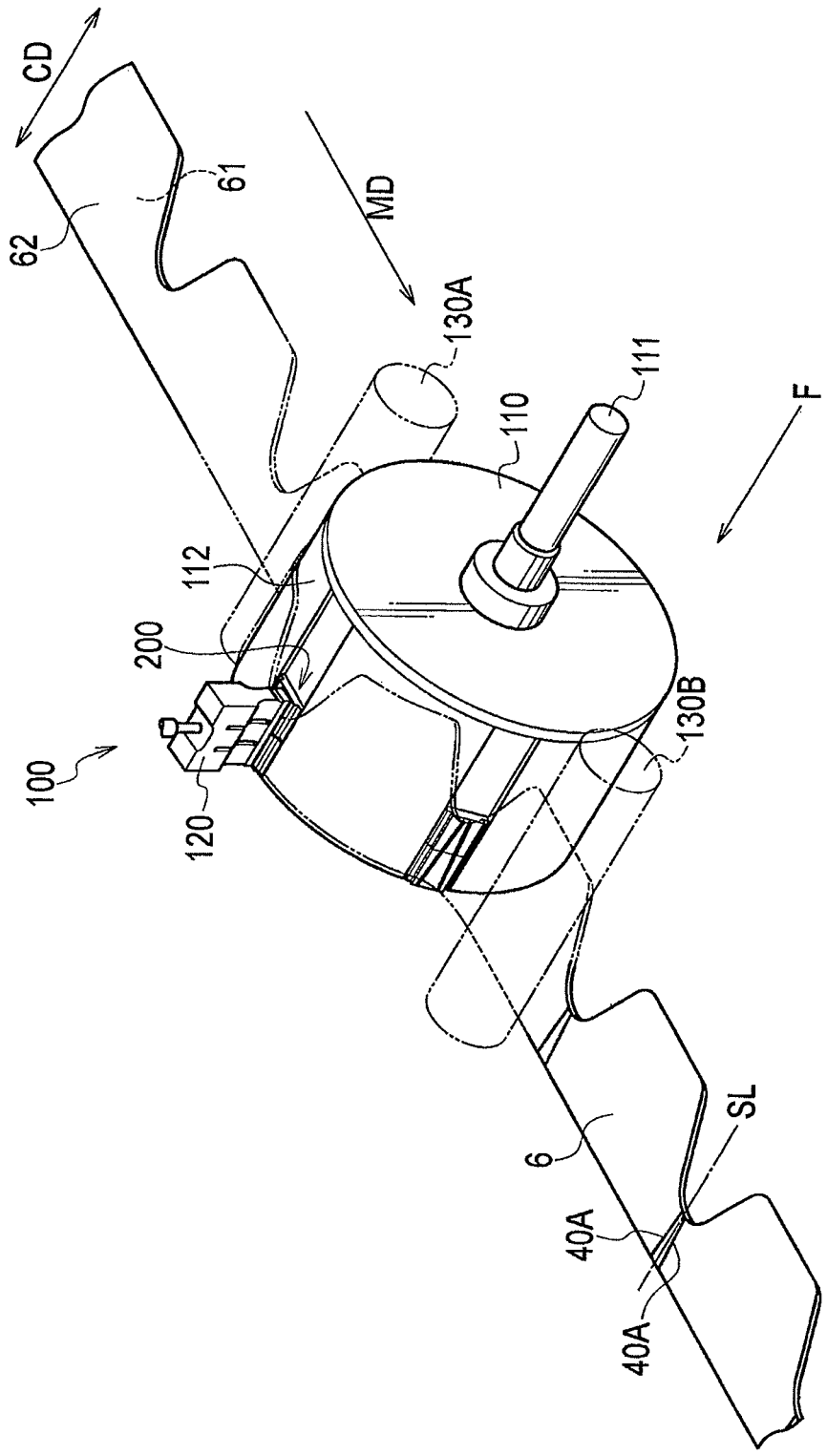
FIG. 3 is a perspective view showing a part of an ultrasonic joining apparatus according to this embodiment.
Figure 4:
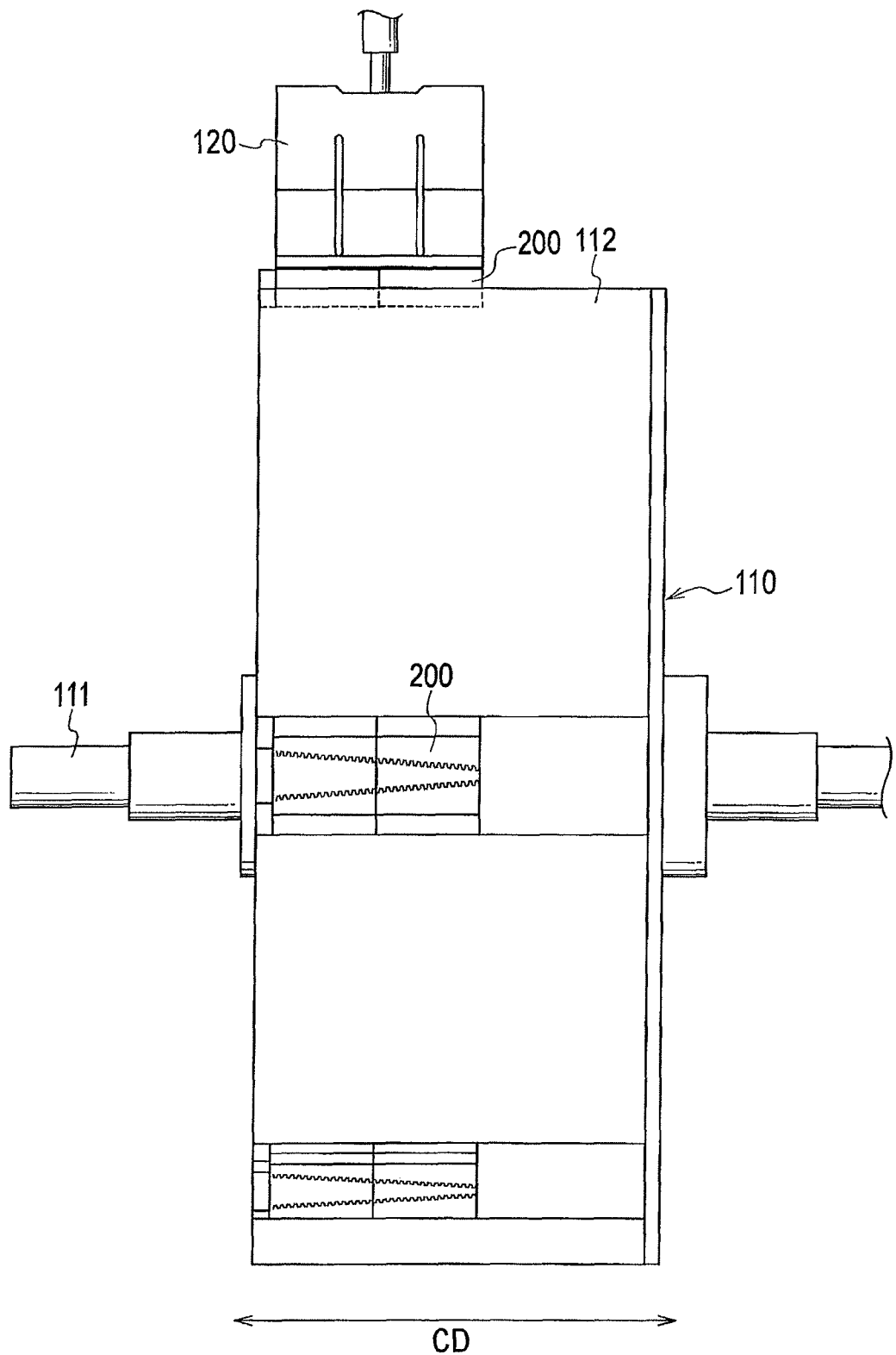
FIG. 4 is a side view showing the ultrasonic joining apparatus according to this embodiment seen from the downstream side.
Figure 5:
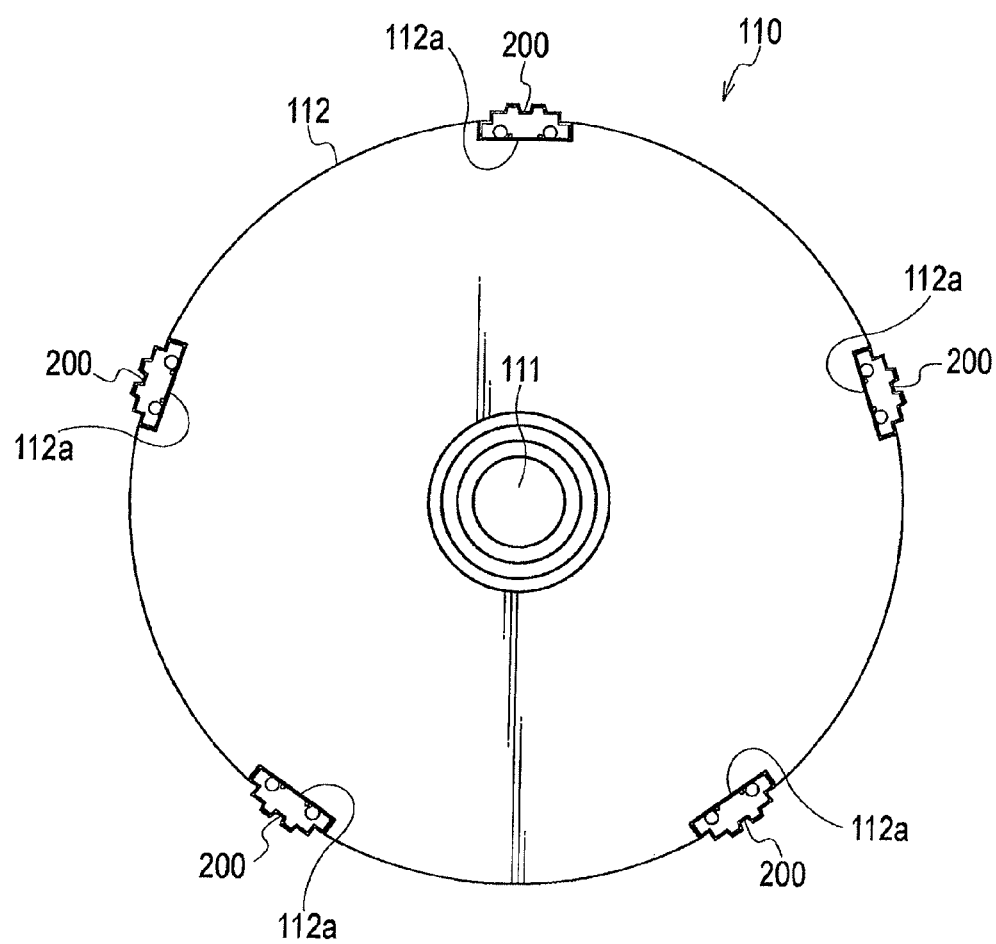
FIG. 5 is a side view showing a rotating drum according to this embodiment seen in a rotational shaft direction.

An ultrasonic joining apparatus 100 is used to perform the joining step S5. A configuration of the ultrasonic joining apparatus 100 according to this embodiment is described below with reference to the drawings. FIG. 3 is a perspective view showing the ultrasonic joining apparatus 100 configured to perform the joining step S5 shown in FIG. 2. The direction of an arrow F in FIG. 3 is equal to that in FIG. 2. FIG. 4 is a side view showing the ultrasonic joining apparatus 100 seen in the machine direction MD from the downstream side. FIG. 5 is a side view showing the ultrasonic joining apparatus 100 seen in a rotational shaft direction. For the sake of explanation, no intermediate web 6 is illustrated in FIGS. 4 and 5.

Figure 6:
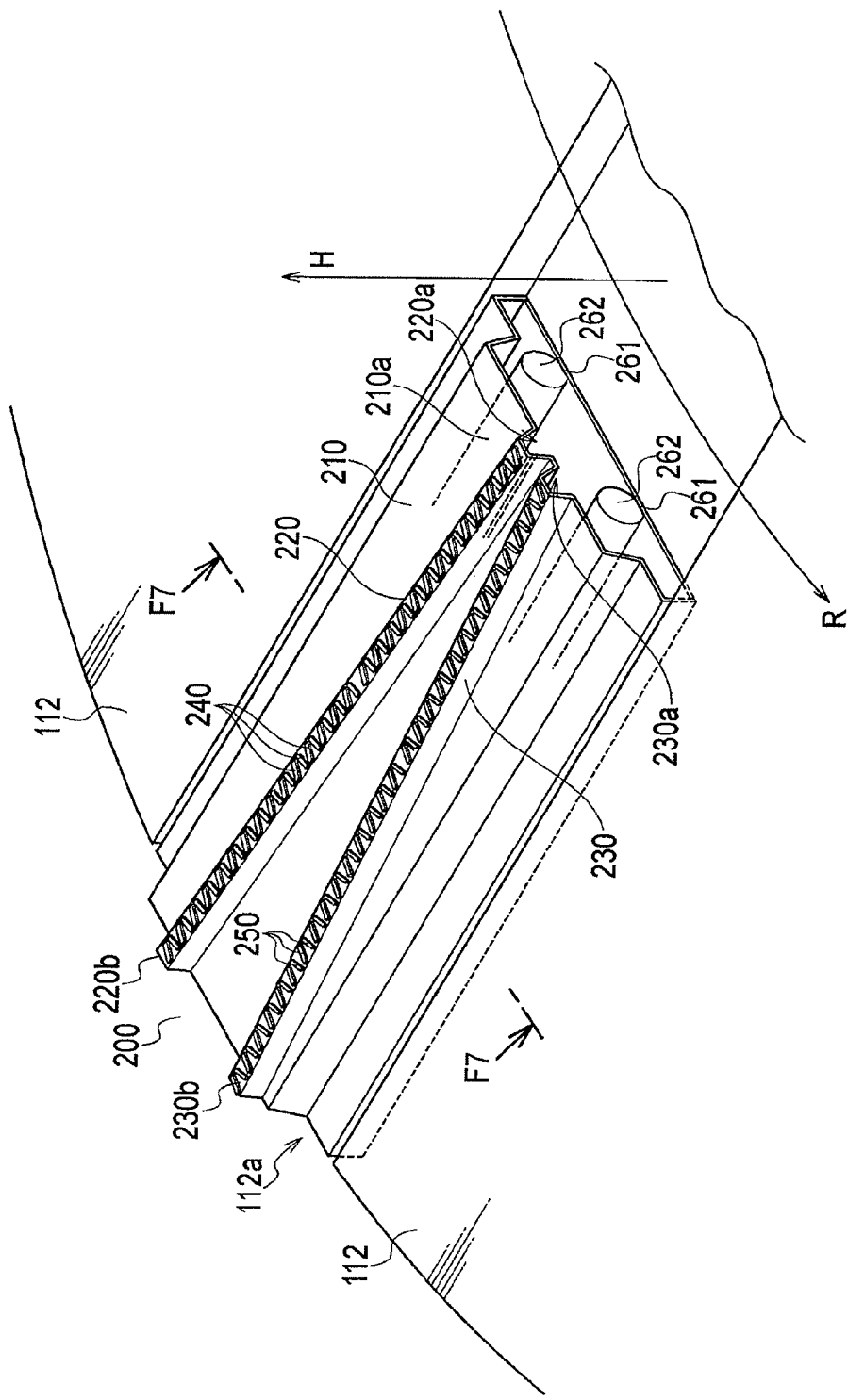
FIG. 6 is a perspective view for explaining an embodiment of an anvil according to this embodiment.
Figure 7:
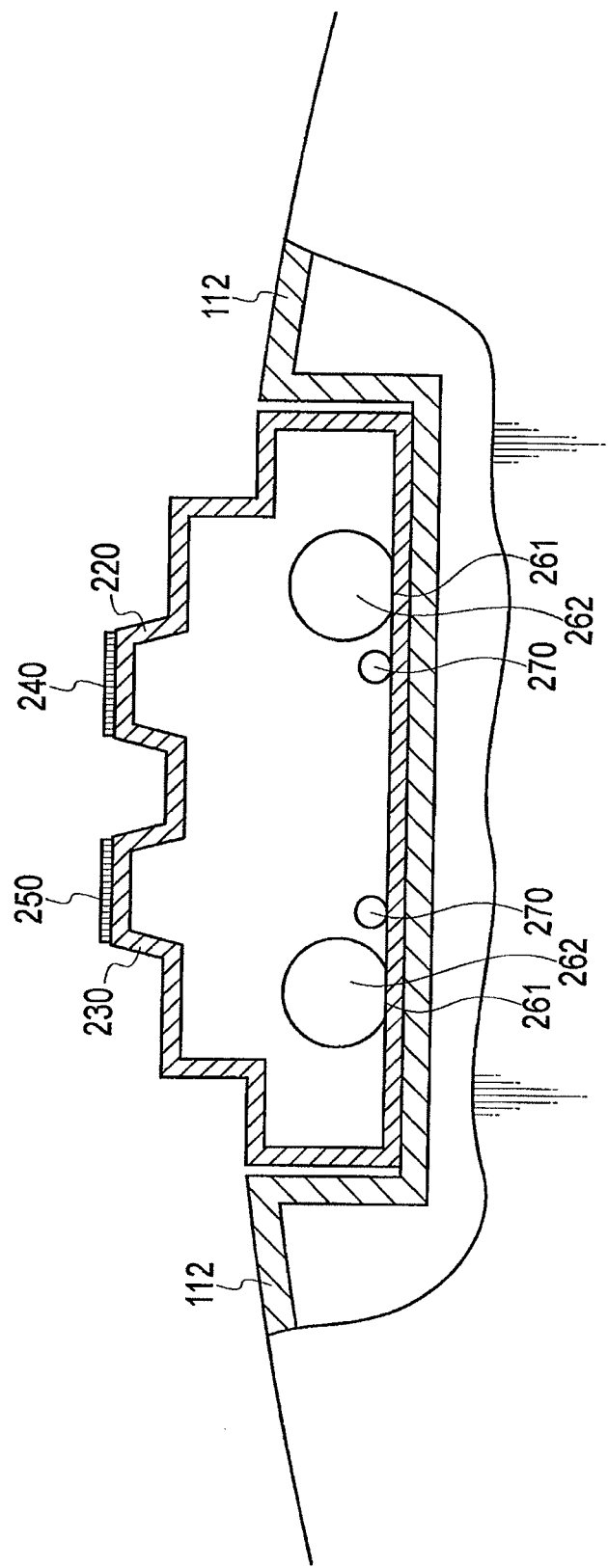
FIG. 7 is a cross-sectional view taken along the line F7-F7 of the anvil shown in FIG. 6.

The ultrasonic joining apparatus 100 includes a rotator 110 and an ultrasonic horn 120 configured to output ultrasonic vibrations. In FIGS. 5 to 7, the rotator 110 is a rotating drum, and is thus called a rotating drum below.

The rotating drum 110 is made of a member to be expanded or contracted by heat. At least the outer peripheral surface 112 of the rotating drum 110 is made of metal. The rotating drum 110 is provided with multiple anvils 200 at predetermined intervals in its rotation direction. Certain anvil attachment portions 112a are provided in the outer peripheral surface 112 of the rotating drum 110. The anvils 200 are installed in the anvil attachment portions 112a, respectively. In the embodiment shown in FIG. 5, the anvil attachment portions 112a are provided in the cylindrically continuous outer peripheral surface 112. The outer peripheral surface 112 constitutes a coupler. Each anvil attachment portion 112a has a portion which is recessed radially inwardly from a surface of the rotating drum 110 to come into contact with the intermediate web 6 (the outer peripheral surface 112). In other words, the anvils 200 are respectively installed in the anvil attachment portions 112a each formed in the outer peripheral surface 112 to have a concave shape.

In this embodiment, five anvils 200 are arranged at equal intervals on the outer peripheral surface 112 of one rotating drum 110. A rotational shaft 111 of the rotating drum 110 extends in parallel with the cross direction CD orthogonal to the machine direction MD in which the manufacturing processes flow. The rotating drum 110 and the ultrasonic horn 120 are arranged to face each other with the intermediate web 6 interposed therebetween, the intermediate web 6 including the web 61 on one side and the web 62 on the other side overlapping with each other.

The ultrasonic horn 120 is coupled to an ultrasonic vibrator via a booster not shown. The ultrasonic horn 120 applies, on the intermediate web 6, ultrasonic vibrations generated by the ultrasonic vibrator and then amplified by the booster. The ultrasonic horn 120 comes into contact with each joint region 40A of the intermediate web 6, and is pressed against one of the anvils 200 described later with the intermediate web 6 interposed therebetween. The contact pressure of the ultrasonic horn 120 against the intermediate web 6 is adjustable.

The ultrasonic joining apparatus 100 is provided with a roll 130A on the upstream side in its flow direction, and a roll 130B on the downstream side in the flow direction. The intermediate web 6 is pressed against the outer peripheral surface 112 of the rotating drum 110 by the rolls 130A and 130B. The ultrasonic joining apparatus 100 causes the anvil 200 and the ultrasonic horn 120 to pinch each joint region 40A of the intermediate web 6 between them, and thereby performs ultrasonic joining on the joint region 40A, the intermediate web 6 being conveyed in the machine direction MD while being pressed against the outer peripheral surface 112 of the rotating drum 110.

When the ultrasonic horn 120 is pressed against the intermediate web 6, the intermediate web 6 is melted by being heated from the inside thereof, and is pressed against protrusions 240 and 250 protruding from projections 220 and 230. As a result, a convexo-concave joint pattern is formed on the intermediate web 6.

(Structure of Anvil)

Next, a structure of each anvil 200 is described by using FIGS. 6 and 7. FIG. 6 is a perspective view of the anvil 200. FIG. 7 is a cross-sectional view taken along the line F7-F7 of the anvil 200. The anvil 200 includes a base 210 and the projections 220 and 230. The base 210 is installed at an anvil attachment position 112a on the outer peripheral surface 112 of the rotating drum 110. The projection 220 protrudes from a front surface 210a of the base 210 in a normal direction H of the rotating drum 110. The projection 220 is formed in a line shape extending in the cross direction CD along the front surface 210a of the base 210.

The projection 220 includes the multiple protrusions 240. Each protrusion 240 protrudes from the front surface of the projection 220 in the normal direction H. On the front surface 210a of the base 210, one end 220a in the cross direction CD of the projection 220 is provided forward of the other end 220b in a rotation direction R.

In the embodiment shown in FIG. 6, the anvil 200 includes a temperature adjustment mechanism 262 configured to adjust a temperature of the rotating drum 110. The temperature adjustment mechanism 262 at least includes a heater configured to generate heat. The anvil 200 also includes a heat transmitter 261 configured to transmit heat generated by the temperature adjustment mechanism 262 to the rotating drum 110. The temperature adjustment mechanism 262 and the heat transmitter 261 are arranged between the rotational axis 111 of the rotating drum 110 and the projection 220. The temperature adjustment mechanism 262 and the heat transmitter 261 are arranged in a portion, of the anvil 200, to be fitted to the portion, of the anvil attachment portion 112a, which is recessed radially inwardly from the outer peripheral surface 112. The anvil 200 also includes a temperature sensor 270 configured to detect a temperature of the anvil attachment portion 112a, of the rotating drum 110, in which the anvil 200 is installed.

The ultrasonic joining apparatus 100 includes a controller (not shown) configured to control a temperature to which the rotating drum 110 should be heated by the temperature adjustment mechanism 262. The controller controls a heat generation amount of the temperature adjustment mechanism 262 on the basis of a detection result by the temperature sensor 270. In the embodiment shown in FIG. 6, the temperature adjustment mechanism 262 and the heat transmitter 261 are installed in each of the multiple anvils 200.

As described above, the ultrasonic joining apparatus 100 includes the temperature adjustment mechanism 262 installed in the anvil 200, and the heat transmitter 261 configured to transmit heat generated by the temperature adjustment mechanism 262 to the rotating drum 110. The temperature adjustment mechanism 262 and the heat transmitter 261 are arranged between the rotational axis 111 of the rotating drum 110 and the projections 220 and 230. This allows reducing heat transmission loss and thus effectively transmitting heat to the rotating drum 110.

Further, the temperature adjustment mechanism 262 and the heat transmitter 261 are installed in each of the multiple anvils 200, and thus a temperature is adjusted by the temperature adjustment mechanism 262 on a per anvil 200 basis. Heat generated by the heater of the temperature adjustment mechanism 262 is transmitted through the heat transmitter 261 to the anvil attachment portion 112a formed in the outer peripheral surface 112 of the metal-made rotating drum 110. In other words, the heat can change the temperature of a portion corresponding to the anvil attachment portion 112a of the rotating drum 110.

In this embodiment, the rotator 110 is in the form of a drum. In the rotator 110, the anvil attachment portions 112a in which the anvils 200 are installed are coupled to one another by the outer peripheral surface 112 (coupler). Heat transmitted through the heat transmitter 261 forms a low-temperature portion and a high-temperature portion in the outer peripheral surface 112 of the rotating drum 110. For this reason, the degree of thermal expansion in a circumferential direction of a metal-made member for forming the rotating drum 110 is different in some portions. This increases the peripheral length of the outer peripheral surface 112 locally, and thereby slightly increases the radial length of the rotating drum 110 in at least the vicinity of each anvil attachment portion 112a.

In this manner, the ultrasonic joining apparatus 100 heats the rotating drum 110 by using the temperature adjustment mechanism 262 installed in each anvil 200. This allows changing a clearance between the ultrasonic horn 120 and each of the projections 240 and 250 of the anvil 200.

Accordingly, the clearance adjustment work is made simpler than the conventional ultrasonic joining apparatus. Further, with the ultrasonic joining apparatus 100, a manufacturing line does not have to be suspended frequently for the clearance adjustment. Further, since the clearance adjustment with the ultrasonic horn 120 is performed on a per anvil 200 basis, the tolerance for the entire intermediate web 6 (i.e., among the absorbent articles 1) can be reduced. As a consequence, ultrasonic joining quality can be enhanced.

Further, each anvil attachment portion 112a has a portion which is recessed radially inwardly from the surface of the rotating drum 110 to come into contact with the intermediate web 6 (the outer peripheral surface 112). The temperature adjustment mechanism 262 and the heat transmitter 261 are installed in the recessed portion.

With the above structure, the temperature adjustment mechanism 262 and the heat transmitter 261 can thermally expand not only the rotating drum 110 but also the anvil 200 itself. Further, the anvil 200, the temperature adjustment mechanism 262, and the heat transmitter 261 are embedded in the rotating drum 110, and thus are prevented from adhesion of paper dust and the like.

(Modification of Rotator)

In the above embodiment, the rotator 110 has been described as the rotating drum having the outer peripheral surface 112. However, the shape of the rotator is not limited to a drum shape. For example, a rotator 300 shown in FIG. 8 includes metal-made ribs 320 extending from the rotational shaft 310 in their respective normal directions H. Each rib 320 has a length at least the same as the width in the cross direction CD of an anvil mounting portion 330. The metal-made anvil mounting portion 330 is attached to the tip of the rib 320. An anvil attachment position 330a is formed in the anvil mounting portion 330. The anvil 200 is attached to the anvil attachment portion 330a.

In the rotator 300 having the anvil mounting portions 330 respectively formed at the tips of their ribs, heat generated by the heater of the temperature adjustment mechanism 262 installed in each anvil 200 is transmitted through the heat transmitter 261 to the anvil attachment position 330a of the corresponding anvil mounting portion 330 formed on the metal-made rotator 300.

The rotator 300 is heated to a predetermined temperature by the heat transmitted through the heat transmitter 261. This thermally expands the corresponding metal-made rib 320 forming the rotator 300, and thus increases the length of the rib 320 from the rotational shaft 310. In other words, the temperature adjustment of the temperature adjustment mechanism 262 directly changes the radial length of the metal-made rib 320, and thus changes a clearance between the ultrasonic horn 120 and each of the projections 240 and 250 of the corresponding anvil 200. Further, the clearance adjustment with the ultrasonic horn 120 can be performed on a per anvil 200 basis by varying a temperature for every anvil 200 installed in the rotator 300.

Figure 8:
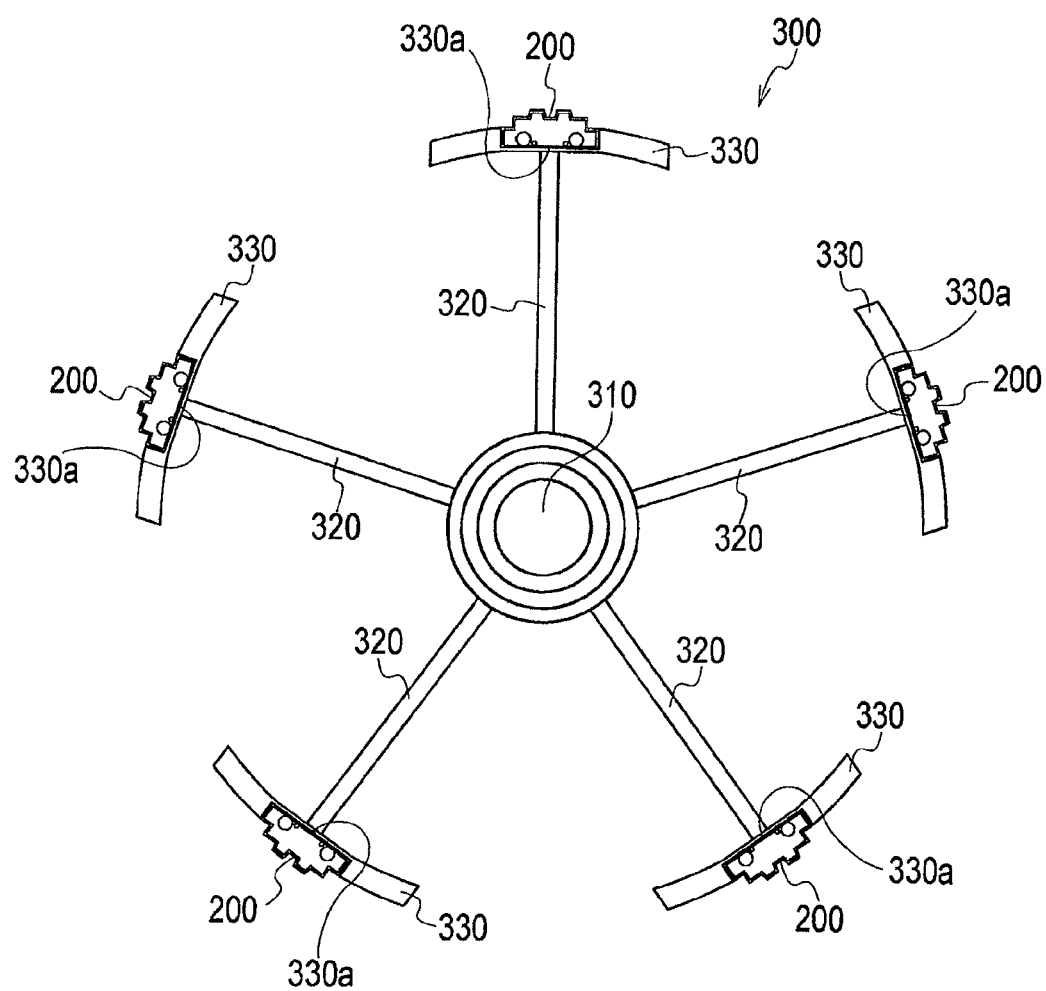
FIG. 8 is a side view showing a modification of the rotating drum.

Note that, in the rotator 300 shown in FIG. 8, the anvil mounting portions 330 may be coupled with one another. Further, in the rotator 300 shown in FIG. 8, the temperature adjustment mechanism 262 may be arranged between each anvil 200 and the rotation center of the rotator 300, that is, may be arranged in each rib 320.

Further, the description has been given of the ribs 320 each having a length the same as the width in the cross direction CD of the anvil mounting portion 330. Alternatively, each rib 320 may be formed of multiple ribs, and does not necessarily have to be continuous in the cross direction CD. Still alternatively, the rib 320 may be in the form of a rod, for example. In the case where the anvil is divided as in Modification 1 of the anvil to be described later, for example, ribs for supporting the respective divided anvil mounting portions may be separately provided.

(Modification 1 of Anvil)

Figure 9:
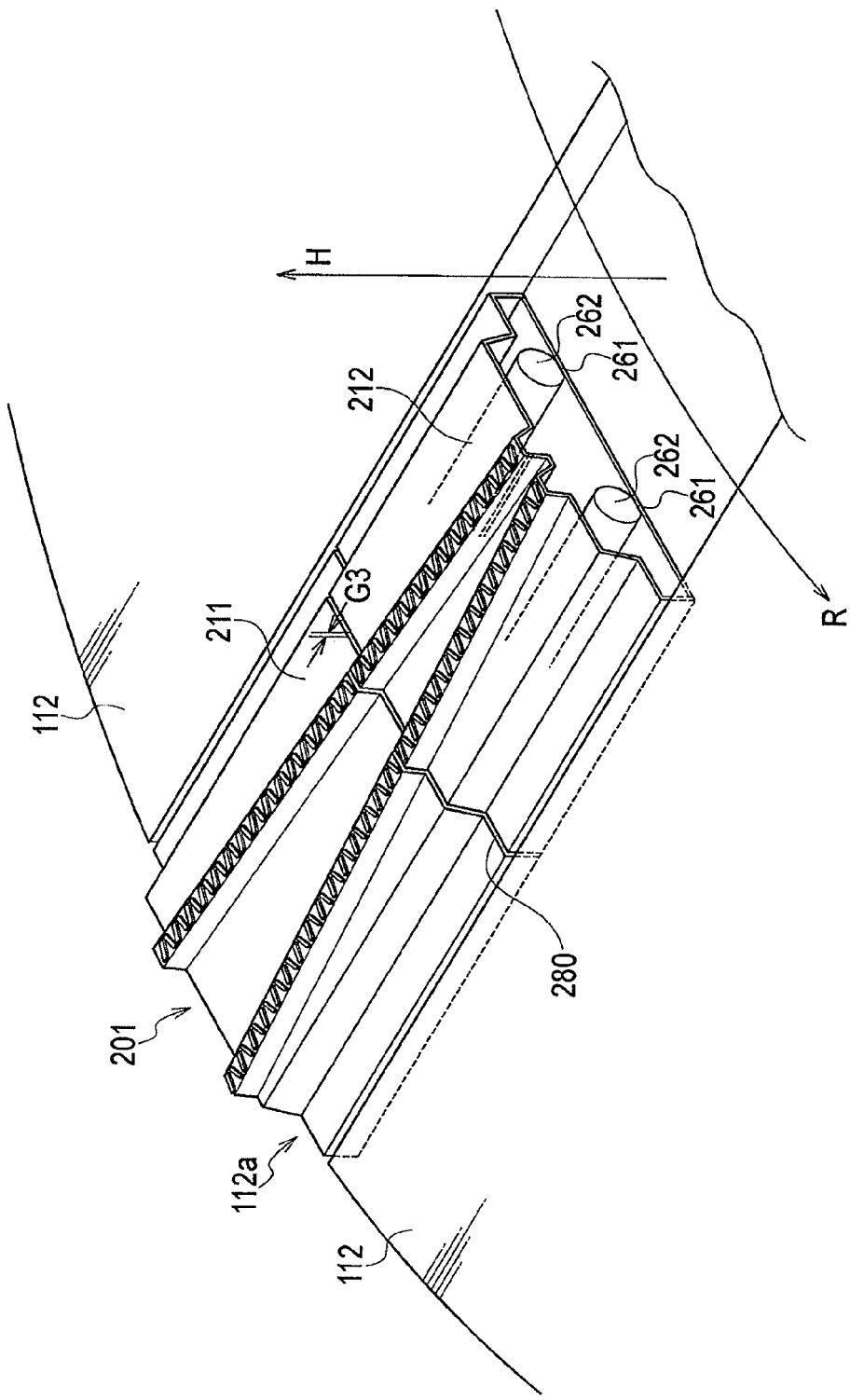
FIG. 9 is a perspective view for explaining Modification 1 of the anvil according to this embodiment.

FIG. 9 shows Modification 1 of the anvil. An anvil 201 may be divided, by a gap 280 (interval G3), into at least two in the rotation direction R at a certain position in the cross direction CD orthogonal to the conveyance direction MD in which the intermediate web 6 is conveyed. The temperature adjustment mechanism 262 and the heat transmitter 261 are installed in each of bases 211 and 212 obtained by the division. The temperature adjustment setting for the bases 211 and 212 may be made separately.

(Modification 2 of Anvil)

Figure 10:
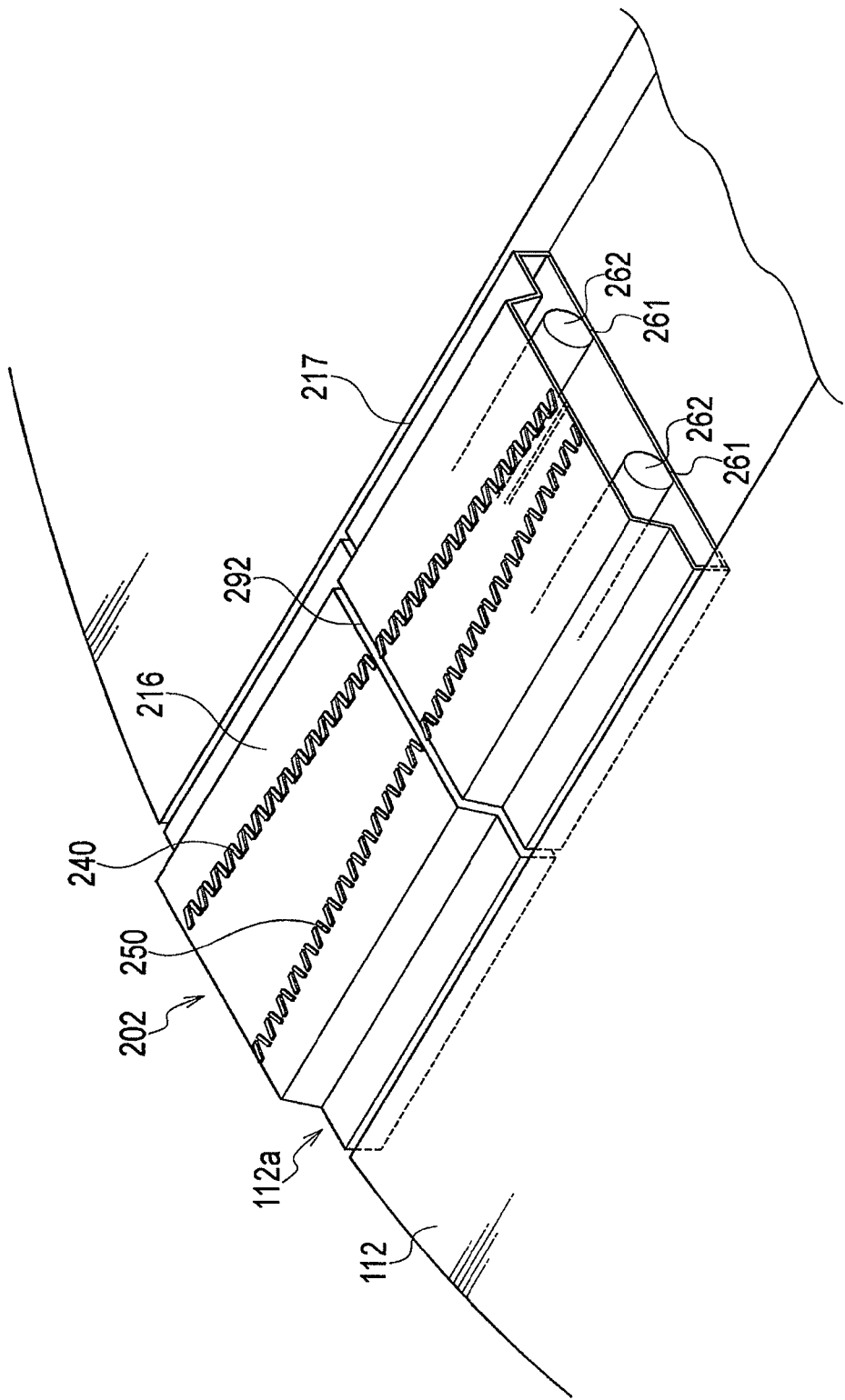
FIG. 10 is a perspective view for explaining Modification 2 of the anvil according to this embodiment.

FIG. 10 shows Modification 2 of the anvil. In an anvil 202, the protrusions 240 and 250 are directly formed on the base. In Modification 2 of FIG. 10, the base is divided into bases 216 and 217 by a gap 292; however, the base does not necessarily have to be divided. The temperature adjustment mechanism 262 and the heat transmitter 261 are installed in each of the bases 216 and 217 obtained by the division. In this modification, the temperature adjustment setting for the bases 216 and 217 may be made separately.

(Other Embodiments)

As described above, the details of the present invention have been disclosed through the embodiment of the present invention. It should not be understood that the description and drawings which constitute part of this disclosure limit the present invention. Based on this disclosure, those skilled in the art may easily come up with various alternative embodiments, examples and operation techniques.

For example, in the above embodiment of the present invention, the description has been given of the case where a joint pattern is formed in the joint regions of the waist lateral-side portions. However, the present invention is not limited to this case. Ultrasonic joining may be applied on any required part.

Further, the description has been provided for the absorbent article 1 formed in combination of the front waistline portion 10, the back waistline portion 20, and the crotch portion 30 (so-called three-piece type). However, the absorbent article 1 is not limited to this structure. Alternatively, the absorbent article 1 may be formed by integrating the front waistline portion 10, the back waistline portion 20, and the crotch portion 30 as a single unit (so-called one-piece type).

Additionally, the description has been provided for the absorbent article 1 as a pants-type disposal diaper. However, the absorbent article 1 is not limited to this. The present invention is applicable to other articles for which the joining step S5 is used (such as an open-type diaper and a napkin). Moreover, needless to say, the structure of the absorbent article 1 is not limited to that described in the above embodiment, but may be set appropriately in accordance with any intended use.

In the embodiment of the present invention, the description has been given of the anvil 200 having the temperature adjustment mechanism 262 configured to heat at least the rotating drum 110 through the heat transmitter 261. Besides the temperature adjustment mechanism 262, the anvil may include a cooling mechanism. The anvil cools the rotating drum through the heat transmitter by carrying heat away from the rotating drum. The provision of the cooling mechanism allows obtaining the effect of suppressing the adhesion, to the anvil, of weld scrap generated by ultrasonic welding, hot melt, and the like.

Further, in the embodiment of the present invention, the description has been given of the anvil attached to the anvil attachment portion of the rotator. Alternatively, the anvil may be integrated into the rotator. According to the present invention, the clearance adjustment for the multiple anvils of the rotator may be performed separately even if the anvils are integrated into the rotator. Thus, the lifetime of the rotator with the anvils built in can be increased even if the degree of wear is different from one anvil to another.

As described above, the present invention naturally includes various embodiments which are not described herein. Accordingly, the technical scope of the present invention should be determined only by the matters to define the invention in the scope of claims regarded as appropriate based on the description.

Note that, the entire content of Japanese Patent Application No. 2009-180195 (filed on Jul. 31, 2009) is incorporated herein by reference.

[Industrial Applicability]

The present invention can provide an ultrasonic joining apparatus capable of reducing the tolerance by adjusting a clearance between each of multiple anvils provided on a rotator and an ultrasonic horn on a per anvil basis, and thereby enhancing ultrasonic joining quality. The present invention can also provide an absorbent article manufacturing apparatus capable of producing a pants-type absorbent article with a stable quality by enhancing ultrasonic joining quality in manufacturing the absorbent article.

The invention claimed is:

1. An ultrasonic joining apparatus, comprising:
a rotator made of a member expansible or contractible by heat;
a plurality of anvils provided at predetermined intervals in a rotation direction of the rotator;
an ultrasonic horn configured to output ultrasonic vibrations; and
a temperature adjustment mechanism configured to adjust a temperature of the rotator, wherein
the rotator and the ultrasonic horn are arranged to face each other with an intermediate web being conveyed therebetween, the intermediate web including a first continuous web and a second continuous web overlapping each other,
each of the plurality of anvils and the ultrasonic horn pinch a corresponding region of the intermediate web to perform ultrasonic joining on the corresponding region, wherein
each of the anvils includes:
a projection protruding in a radial direction of the rotator;
a plurality of protrusions protruding from the projection in the radial direction; and
a heat transmitter configured to transmit heat generated by the temperature adjustment mechanism to the rotator,
the temperature adjustment mechanism and the heat transmitter are arranged between a rotational axis of the rotator and the projection,
the temperature adjustment mechanism and the heat transmitter are arranged in each of the plurality of anvils, and
the temperature adjustment mechanism is configured to adjust the temperature of the rotator on a per anvil basis.

2. The ultrasonic joining apparatus according to claim 1, wherein
the rotator includes anvil attachment portions to which the respective anvils are attached,
the anvil attachment portions are coupled to one another by a coupler, and
the coupler forms an outer peripheral surface of the rotator.

3. The ultrasonic joining apparatus according to claim 1, wherein
the rotator includes anvil attachment portions to which the respective anvils are attached, and
the anvil attachment portions are independent of one another, and coupled to a coupler extending radially from a rotational shaft of the rotator.

4. The ultrasonic joining apparatus according to claim 2, wherein
each of the anvil attachment portions has a recessed portion which is recessed radially inwardly from a surface of the rotator to come into contact with the intermediate web, and
the temperature adjustment mechanism and the heat transmitter are arranged in the recessed portion.

5. The ultrasonic joining apparatus according to claim 2, wherein
each of the anvils is divided into at least two sections in the rotation direction of the rotator at a position in a cross direction orthogonal to a conveyance direction in which the intermediate web is conveyed, and
the temperature adjustment mechanism and the heat transmitter are arranged in each of the sections of the divided anvil.

6. An absorbent article manufacturing apparatus, comprising:
a rotator made of a member expansible or contractible by heat;
a plurality of anvils provided at predetermined intervals in a rotation direction of the rotator;
an ultrasonic horn configured to output ultrasonic vibrations; and
a temperature adjustment mechanism configured to adjust a temperature of the rotator, wherein
the rotator has a rotational shaft extending in parallel with a cross direction orthogonal to a machine direction in which manufacturing processes flow,
the rotator and the ultrasonic horn are arranged to face each other with an intermediate web interposed therebetween, the intermediate web including a first web to form a front waistline portion of an absorbent article and a second web to form a back waistline portion of the absorbent article, the first web and the second web overlapping each other, the absorbent article includes:
the front waistline portion to be fitted to a front waist of a wearer;
the back waistline portion to be fitted to a back waist of the wearer;
a crotch portion to be fitted to a crotch of the wearer; and
leg-surrounding opening portions which open at both sides of the crotch portion, and
each of the anvils and the ultrasonic horn pinch a corresponding region of the intermediate web, which is conveyed in the machine direction, to perform ultrasonic joining on the corresponding region, and the temperature adjustment mechanism is arranged in each of the anvils, each of the anvils includes:
- a projection protruding in a radial direction of the rotator;
- a plurality of protrusions protruding from the projection in the radial direction; and
- a heat transmitter configured to transmit heat generated by the temperature adjustment mechanism to the rotator.

7. The absorbent article manufacturing apparatus according to claim 6, wherein the temperature adjustment mechanism and the heat transmitter are arranged between the rotational shaft of the rotator and the projection.

8. The absorbent article manufacturing apparatus according to claim 6, wherein
the temperature adjustment mechanism is configured to adjust the temperature of the rotator on a per anvil basis.

9. The absorbent article manufacturing apparatus according to claim 6, wherein
the rotator includes anvil attachment portions to which the respective anvils are attached, the anvil attachment portions are coupled to one another by a coupler, each of the anvil attachment portions has a recessed portion which is recessed radially inwardly from a surface of the rotator to come into contact with the intermediate web, and the temperature adjustment mechanism and the heat transmitter are arranged in the recessed portion.

10. The absorbent article manufacturing apparatus according to claim 6, wherein
each of the anvils is divided into at least two sections in the rotation direction of the rotator at a position in the cross direction orthogonal to the machine direction in which the intermediate web is conveyed, and the temperature adjustment mechanism and the heat transmitter are arranged in each of the sections of the divided anvil.

\* \* \* \* \*